United States Patent [19]
De Boer et al.

[11] Patent Number: 5,397,703
[45] Date of Patent: Mar. 14, 1995

[54] METHOD FOR GENERATION OF ANTIBODIES TO CELL SURFACE MOLECULES

[75] Inventors: Mark De Boer, Almere, Netherlands; Leah B. Conroy, Pacifica, Calif.

[73] Assignee: Cetus Oncology Corporation, Emeryville, Calif.

[21] Appl. No.: 910,222

[22] Filed: Jul. 9, 1992

[51] Int. Cl.$^6$ .............. C12N 15/02; C12N 15/06; A61K 39/00
[52] U.S. Cl. .............. 435/172.2; 435/172.3; 530/389.1
[58] Field of Search ........... 435/172.3, 240.27, 70.21, 435/172.2; 424/93 B

[56] References Cited
PUBLICATIONS

DiSanto, et al.; Journal of Immunological Methods, vol. 141, pp. 123–131; 1991.
Webb, et al.; Proceedings of the National Academy of Sciences USA, vol. 86, pp. 7731–7735; 1989.
Golub; *Immunology A Synthesis*; Published by Sinauer Associates, Inc.; Sunderland, Mass., 1987, pp. 19–20.
Dharakul, T., et al., "Immunization with Baculovirus—Expressed Recombinant Rotavirus Proteins VP1, VP4, VP6, and VP7 Induces CD8+ T Lymphocytes That Mediate Clearance of Chronic Rotavirus Infection in SCID Mice," J. Virol. 65(11):5928–5932 (1991).
DiSanto, J. P., et al., "Generation of anti–human CD8β–specific antibodies using transfectants expressing mixed–species CD8 heterodimers," J. Immunolog. Methods 141:123–131 (1991).
Miller, L. K., "Chapter 23: Baculoviruses for Foreign Gene Expression in Insect Cells," in *Vectors: A Survey of Molecular Cloning Vectors and Their Uses* (Rodriguez, R. L., et al., eds.,. Butterworths 1988, pp. 457–465).
Sekine, H., et al., "Expression of human papillomavirus type 6b E2 gene product with DNA-binding activity in insect (*Bombyx Mori*) cells using a baculovirus expression vector," Gene 65(2):187–193 (1988).
Smith, G. E., et al., "Modification and secretion of human interleukin 2 produced in insect cells by a baculovirus expression vector," Proc. Natl. Acad. Sci. USA 82:8404–8408 (1985).
Takehara, K., et al., "Co—expression of the hepatitis B surface and core antigens using baculovirus multiple expression vectors," J. Gen. Virol. 69(Pt.11):2763–2777 (1988).
Urakawa, T., et al., "Synthesis of immunogenic, but non-infectious, poliovirus particles in insect cells by a baculovirus expression vector," J. Gen. Virol. 70(Pt.6):1453–1463 (1989).
Webb, N. R., et al., "Cell-surface expression and purification of human CD4 produced in baculovirus-infected insect cells," Proc. Natl. Acad. Sci. USA 86:7731–7735 (1989).

*Primary Examiner*—George C. Elliott
*Attorney, Agent, or Firm*—Thomas C. Meyers; Paul B. Savereide; Robert P. Blackburn

[57] ABSTRACT

The present invention relates to a method of generating antibodies directed against cell surface antigens. The method uses as immunogen recombinant insect cells into which have been transfected coding regions for a molecule containing a cell surface antigen. Host animals are immunized with these transfected insect cells to generate antibodies directed against the cell surface antigen. Antibody-producing cells from the host animal are used to generate monoclonal antibody-producing hybridoma cells. Sera and hybridoma supernatants can be tested for the presence of antibodies against the surface antigen, using the transfected cells in a screening assay.

17 Claims, 8 Drawing Sheets

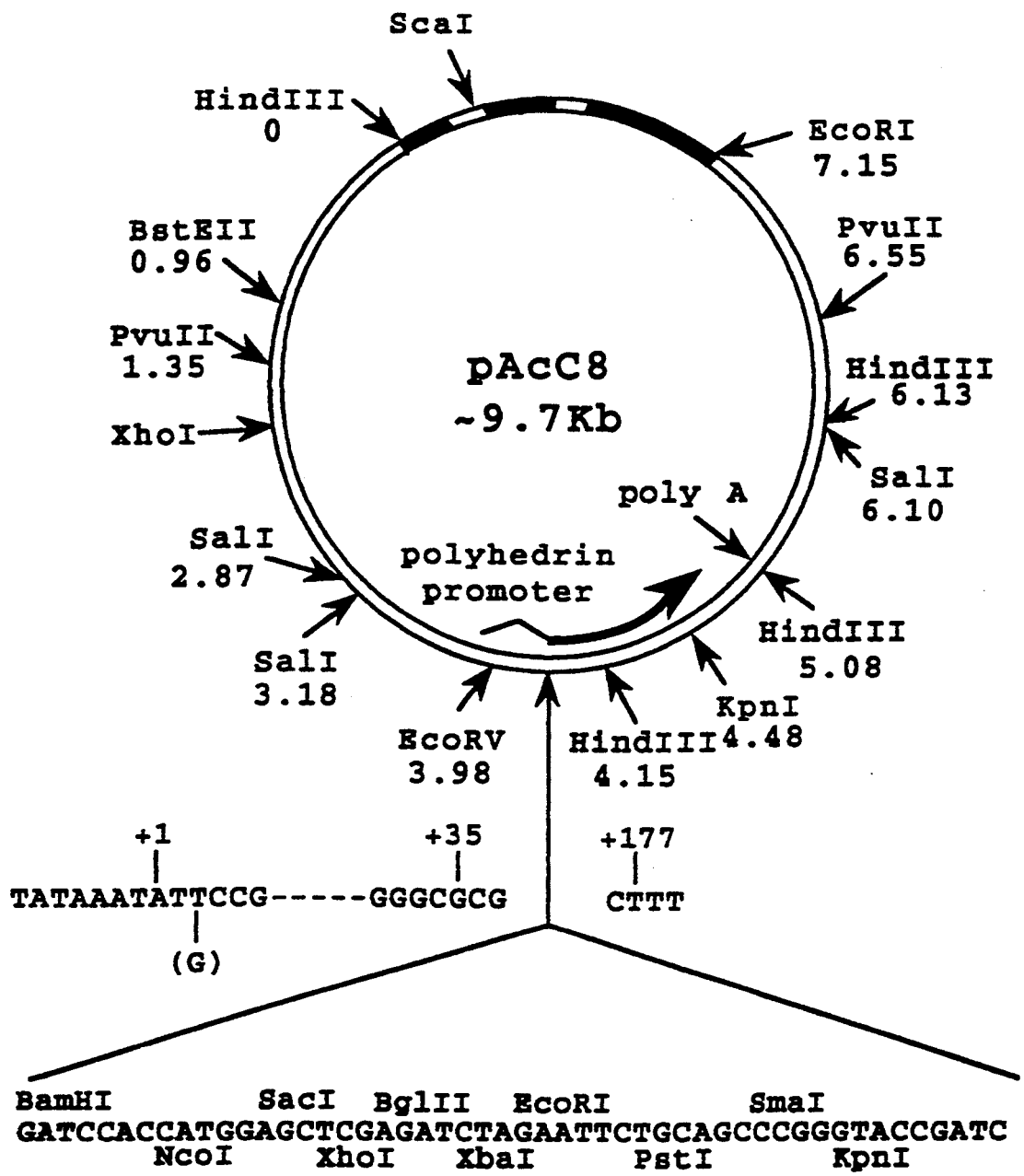
FIG. IA

Full length B7:

Forward  MR67  5'-GCG CTGCAG CATCTGAAGCCATGGGCC-3'  (307-324)

Backward MR68  5'-CGC GGTACC TTGCTTCTGCGACACTG-3'  (1182-1199)

Soluble B7:

Forward  MR67  5'-GCG CTGCAG CATCTGAAGCCATGGGCC-3'  (307-324)

Backward MR145 5'-GCGC GGTACC TTACTCCATGGGCATGTATTCCTCTTCCTCGTTATCAGGAAAATGCTGTTG-3' (1022-1042)

Full length CD40:

Forward  MR108 5'-GCGT AGATCT GGTCTCACCTCGCCATGGTTCG-3'  (34-55)

Backward MR112 5'-GCGT GGTACC CCACACTCCTGGGTGGGTGCAGCC-3'  (882-905)

Soluble CD40:

Forward  MR108 5'-GCGT AGATCT GGTCTCACCTCGCCATGGTTCG-3'  (34-55)

Backward MR150 5'-GCGT GGTACC TTACTCCATGGGCATGTATTCCTCTTCCTCATCAGTCTTGTTTGTGCCTGC-3' (575-596)

FIG. 2

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( C ) INDIVIDUAL ISOLATE: Forward Primer for B7, MR67, Figure 2

( x i ) SEQUENCE DESCRIPTION: SEQ ID NO:1:

GCGCTGCAGC ATCTGAAGCC ATGGGCC        27

( 2 ) INFORMATION FOR SEQ ID NO:2:

( i ) SEQUENCE CHARACTERISTICS:
   ( A ) LENGTH: 27 base pairs
   ( B ) TYPE: nucleic acid
   ( C ) STRANDEDNESS: single
   ( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
   ( C ) INDIVIDUAL ISOLATE: Backward Primer for B7, MR68

( x i ) SEQUENCE DESCRIPTION: SEQ ID NO:2:

CGCGGTACCT TGCTTCTGCG GACACTG        27

( 2 ) INFORMATION FOR SEQ ID NO:3:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
      ( C ) INDIVIDUAL ISOLATE: Forward Primer for Soluble B7,
         MR67

( x i ) SEQUENCE DESCRIPTION: SEQ ID NO:3:

GCGCTGCAGC ATCTGAAGCC ATGGGCC        27

( 2 ) INFORMATION FOR SEQ ID NO:4:

( i ) SEQUENCE CHARACTERISTICS:
      ( A ) LENGTH: 61 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
      ( C ) INDIVIDUAL ISOLATE: Backward Primer for Soluble B7,
         MR145

( x i ) SEQUENCE DESCRIPTION: SEQ ID NO:4:

GCGCGGTACC TTACTCCATG GGCATGTATT CCTCTTCCTC GTTATCAGGA AAATGCTGTT        60
G        61

( 2 ) INFORMATION FOR SEQ ID NO:5:

( i ) SEQUENCE CHARACTERISTICS:
      ( A ) LENGTH: 32 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( C ) INDIVIDUAL ISOLATE: Forward Primer for CD40, MR108

( x i ) SEQUENCE DESCRIPTION: SEQ ID NO:5:

GCGTAGATCT GGTCTCACCT CGCCATGGTT CG                      32

( 2 ) INFORMATION FOR SEQ ID NO:6:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
    ( C ) INDIVIDUAL ISOLATE: Backward Primer for CD40, MR112

( x i ) SEQUENCE DESCRIPTION: SEQ ID NO:6:

GCGTGGTACC CCACACTCCT GGGTGGGTGC AGCC                    34

( 2 ) INFORMATION FOR SEQ ID NO:7:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( C ) INDIVIDUAL ISOLATE: Forward Primer for Soluble CD40, MR108

( x i ) SEQUENCE DESCRIPTION: SEQ ID NO:7:

GCGTAGATCT GGTCTCACCT CGCCATGGTT CG                      32

( 2 ) INFORMATION FOR SEQ ID NO:8:

( i ) SEQUENCE CHARACTERISTICS:
    ( A ) LENGTH: 61 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
    ( C ) INDIVIDUAL ISOLATE: Backward Primer for Soluble CD40, MR150

( x i ) SEQUENCE DESCRIPTION: SEQ ID NO:8:

GCGTGGTACC TTACTCCATG GGCATGTATT CCTCTTCCTC ATCAGTCTTG TTTGTGCCTG    60
C                                                                   61

METHOD FOR GENERATION OF ANTIBODIES TO CELL SURFACE MOLECULES

FIELD OF THE INVENTION

The present invention relates to a method of generating antibodies directed against membrane-associated antigen molecules. More specifically, the present invention describes methods of using these membrane-associated antigens for the immunization of a host animal and for screening antibodies isolated from the host animal.

References

Ausubel, F. M. et al. *Current Protocols in Molecular Biology*, John Wiley and Sons, Media, Pa.

Bohinski, R. C., *Modern Concepts in Biochemistry*, Second Edition, Allyn and Bacon, Inc.

Carroll, W. P., Thielemans, K., Dilley, J., and Levy, R. (1986) J. Immunol. Methods 89: 61.

Chirgwin, J. M., et al., Biochemistry 17:5294 (1979).

Clark, E. A., et al., Proc. Natl. Acad. Sci. U.S.A. 83:4494 (1986).

Coon, J. S., et al. (editors), *Diagnostic Flow Cytometry*, Academy of Pathology Inc. (1991).

Crea, R., U.S. Pat. No. 4,888,286, issued Dec. 9, 1989.

de Boer, M., et al., J. Immunol. Methods 113:143 (1988).

DeGroot, C., et al., Lymphokine Research 9:321 (1990).

DiSanto, J. P., et al., J. Immunol. Methods 141:123 (1991).

Eaton, M. A. W., et al., U.S. Pat. No. 4,719,180, issued Jan. 12, 1988.

Freedman, A. S., et al., J. Immunol. 139:3260 (1987).

Freeman, G. J., et al., J. Immunol. 143:2714 (1989).

Harlow, E., et al., *Antibodies: A Laboratory Manual*, Cold Spring Harbor Laboratory Press (1988).

Huynh, T. V., et al., in "DNA Cloning, Volume 1," ed. D. M. Glover, Washington, D.C.: IRL Press, 1985 (Chapter 2).

Keren, D. F., (editor), *Flow Cytometry in Clinical Diagnosis*, American Society of Clinical Pathologists (1989).

Luckow, V. A., et al., "Cloning and expression of heterologous genes in insect cells with baculovirus vectors", in *Recombinant DNA Technology and Applications* (C. Ho., A. Prokop, and R. Bajpai, eds.) McGraw-Hill, New York (1991).

Luckow, V. A., et al., Virology 170:31 (1989).

Maiorella, B., et al., Biotechnology 6:1406 (1988).

Maniatis, T., et al., *Molecular Cloning: A Laboratory Manual*, Cold Spring Harbor Laboratories, Cold Spring Harbor, N.Y. (1982).

Matsuura, Y., et al., J. Gen. Vir. 68(pt.5):1233-1250 (1987).

Miller, L. K. (1988) in *Vectors: A Survey of Molecular Cloning Vectors and Their Uses*, Rodriguez, R. L. and Denhardt, D. T., eds. Butterworths, Boston.

Mishell, B. B. and Shiigi, S. M., eds. (1980) *Selected Methods in Cellular Immunology*, W. H. Freeman and Co., San Francisco.

Mullis, K. B., U.S. Pat. No. 4,683,202, issued Jul. 28, 1987.

Mullis, K. B., et al., U.S. Pat. No. 4,683,195, issued Jul. 28, 1987.

Nyunoya, H., et al., AIDS Res. Hum. Retrovir. 6 (11):1311-1321 (1990).

Paulie, S., et al., Cancer Immunol. Immunother. 20:23 (1985).

Perkins, S. et al (1989) in Borrebaeck, C. A. K., Hagen, I. (eds) *Electromanipulation in Hybridoma Technology, A Laboratory Manual*, Stockton Press, New York.

Perkins, S., Zimmerman, U., Foung, S. K. H. (1991) Hum. Antibod. Hybridomas 2: 155-159.

Powers, L. W., *Diagnostic Hematology: Clinical and Technical Principles*, C. V. Mosby Company (1989).

Sambrook, J., et al., In *Molecular Cloning: A Laboratory Manual*, Cold Spring Harbor Laboratory Press, Vol. 2 (1989).

Saiki, R. K., et al., Science 230:1350 (1985).

Saiki, R. K., et al., Science 239:487 (1988).

Sekine, H., et al., Gene 65(2):187-193 (1988).

Stamenkovic, I., et al., EMBO J. 8:1403 (1989).

Summers, M. D., et al., *A manual of Methods for Baculovirus Vectors and Insect Cell Culture Procedures*, Texas Agricultural Experimental Station Bulletin, No. 1555 (1987).

Takehara, K., et al., J. Gen. Virol. 69(pt.11):2763-2777 (1988).

Valle, A., et al., Immunology 69:531 (1990).

Webb, N. R., et al., Technique 2:173 (1990).

Webb, N. R., et al., Proc. Natl. Acad. Sci. U.S.A. 86:7731 (1989).

Wu, A. Z., et al., Chin. J. Biotech. 6(4):237-242 (1990).

Yokochi, T., et al., J. Immunol. 128:823 (1982).

Yoshio, T., et al., U.S. Pat. No. 4,849,350, issued Jul. 18, 1989.

BACKGROUND OF THE INVENTION

Monoclonal antibodies have proven to be powerful tools in immunological research. In general, monoclonal antibodies can be produced using impure antigens as immunogens, provided that there is available a screening assay which distinguishes antibodies directed against the antigen of interest from antibodies directed against other antigens present in the immunogenic composition. When the antigen of interest is a cell surface molecule, it is desirable to use cells or membrane fractions containing the molecule of interest as immunogens in order to preserve the conformational constraints provided by a membrane environment.

Immunizing mice with whole cells usually yields a strong immune response which generates antibodies to a large number of different molecules. This broad immune response precludes the use of the immunogen cells in subsequent screening for specific antibody production by hybridoma clones derived from the mouse spleen or lymphocyte cells.

Furthermore, when the antigen of interest is expressed at low density, it is likely that the frequency of mouse B cells specific for the antigen will be relatively low. This low frequency necessitates the screening of large numbers of hybridoma clones to identify a clone which produces antibodies directed against the antigen of interest.

Syngeneic murine fibroblasts expressing human cell surface antigens have been used to immunize mice for specific antibody production (DiSanto et al., 1991). When injected into the appropriate mouse strain, the background antigen proteins present on the fibroblasts should not be immunogenic, so that the immune response should be focused on the xenogeneic recombinant protein. However, this approach requires the construction of specific recombinant cells for each species or strain in which antibody production is desired.

The present invention provides a method for generating antibody-producing cells, where the antibodies have binding specificity for a specific cell-surface molecule: this method overcomes the limitations of the above-described methods.

SUMMARY OF THE INVENTION

The present invention provides a method of generating immortalized cell lines capable of producing a monoclonal antibody specifically reactive against a selected membrane associated antigen. In the method, the membrane-associated antigen is produced on the cell surface of insect cells, typically via recombinant expression of antigen coding sequences using baculoviral vectors. These insect cells are injected into a host animal. Cells capable of producing antibodies directed against the membrane-associated antigen are recovered; such cells are immortalized for growth in cell culture. The immortalized cells are screened for production of antibodies specific to the membrane-associated antigen. The screening is typically accomplished using a binding assay employing non-insect cells having the membrane-associated antigen on the surface. Immortalized cells producing antibodies which bind to the membrane-associated antigen on the surface of said non-insect cells are selected.

In one embodiment, DNA sequences encoding the membrane-associated antigen are inserted operatively into a baculoviral vector suitable for expression of the antigen in selected insect cells. The vector carrying the DNA sequences encoding the antigen are introduced into insect cells, for example, by transfection with the vector. Insect cells, transformed with the vector, are selected which produce the membrane-associated antigen on the cell surface.

One method of isolating target DNA sequences, encoding the membrane-associated antigen of interest, is using the polymerase chain reaction employing either DNA or RNA templates containing the target DNA sequences.

Insect cells useful in the practice of the present invention can be obtained from *Spodoptera frugiperda*.

Commonly used host animal cells, capable of producing antibody molecules directed against the membrane associated antigen, are splenic cells or lymphocytes: immortalization of the host animal cells is accomplished by standard procedures.

In one embodiment of the present invention, the host animal is a mouse.

In the above described method, a number of non-insect cells, having the membrane-associated antigen on the surface, can be employed, including human cells. Such non-insect cells can be primary or cultured cells. In one embodiment, the non-insect cells can be cultured human lymphocytes: in particular, transformed B cells.

In the method of the present invention, useful membrane-associated antigens include the following: human cell surface proteins; antigenic marker proteins for a peripheral blood mononuclear cells, for example, CD40 or B7; and viral antigenic proteins present on the surface of a human cell.

The present invention also describes a method of producing sera containing antibodies specific against a selected membrane-associated antigen, where the membrane-associated antigen is present on the cell surface of insect cells, the cells are injected into a host animal, and sera from the animal are screened for the presence of antibodies specific to the membrane-associated antigen. Such screening typically employs a binding assay using non-insect cells having the membrane-associated antigen on the cell surface.

Sera and hybridoma supernatants can also be tested for the presence of antibodies against a selected membrane-associated antigen using, in a screening assay, recombinant insect cells expressing the antigen.

BRIEF DESCRIPTION OF THE FIGURES

FIGS. 1A and 1B show a schematic representation of the baculoviral transfer vector pAcC8 and the sequence of the multiple cloning site. FIG.(1A) shows a schematic representation of the generation of Sf9 cells which express human CD40 or B7 antigen according to the method of the present invention (1B).

FIG. 2 shows the sequences of polymerase chain reaction primers used in the preparation of coding regions for human CD40 and human B7 antigens. These primers were constructed on the basis of the published complete DNA coding sequences for antigens B7 and CD40 (Freeman et al., 1989; Stamenkovic et al., 1989).

FIG. 5A shows the results of staining ARC EBV transformed cells with serum from a mouse immunized with B7 expressing Sf9 cells (solid line) or with normal mouse serum (dotted line). FIG. 5B shows the results of staining ARC EBV transformed cells with serum from a mouse immunized with CD40 expressing Sf9 cells (solid line) or with normal mouse serum (dotted line). FIG. 5C shows the results of staining ARC EBV transformed cells with serum from a mouse immunized with control Sf9 cells (solid line) or with normal mouse serum (dotted line).

FIG. 6A shows the results of staining with B7-24 (dotted line) or secondary antibody only (solid line). FIG. 6B shows the results of staining with B7-24 alone (dotted line) or B7-24 preincubated with soluble B7 (solid line). FIG. 6C shows the results of staining with B7-24 alone (dotted line) or B7-24 preincubated with soluble CD40. FIG. 6D shows the results of staining with CD403A8 (dotted line) or second antibody alone (solid line). FI. 6E shows the results of staining with CD407A8 alone (dotted line) or CD403A8 preincubated with soluble B7 (solid line). FIG. 6F shows the results of staining with CD403A8 alone (dotted line) or preincubated with soluble CD40 (solid line).

DETAILED DESCRIPTION OF THE INVENTION

I. Definitions

Figure 1B:
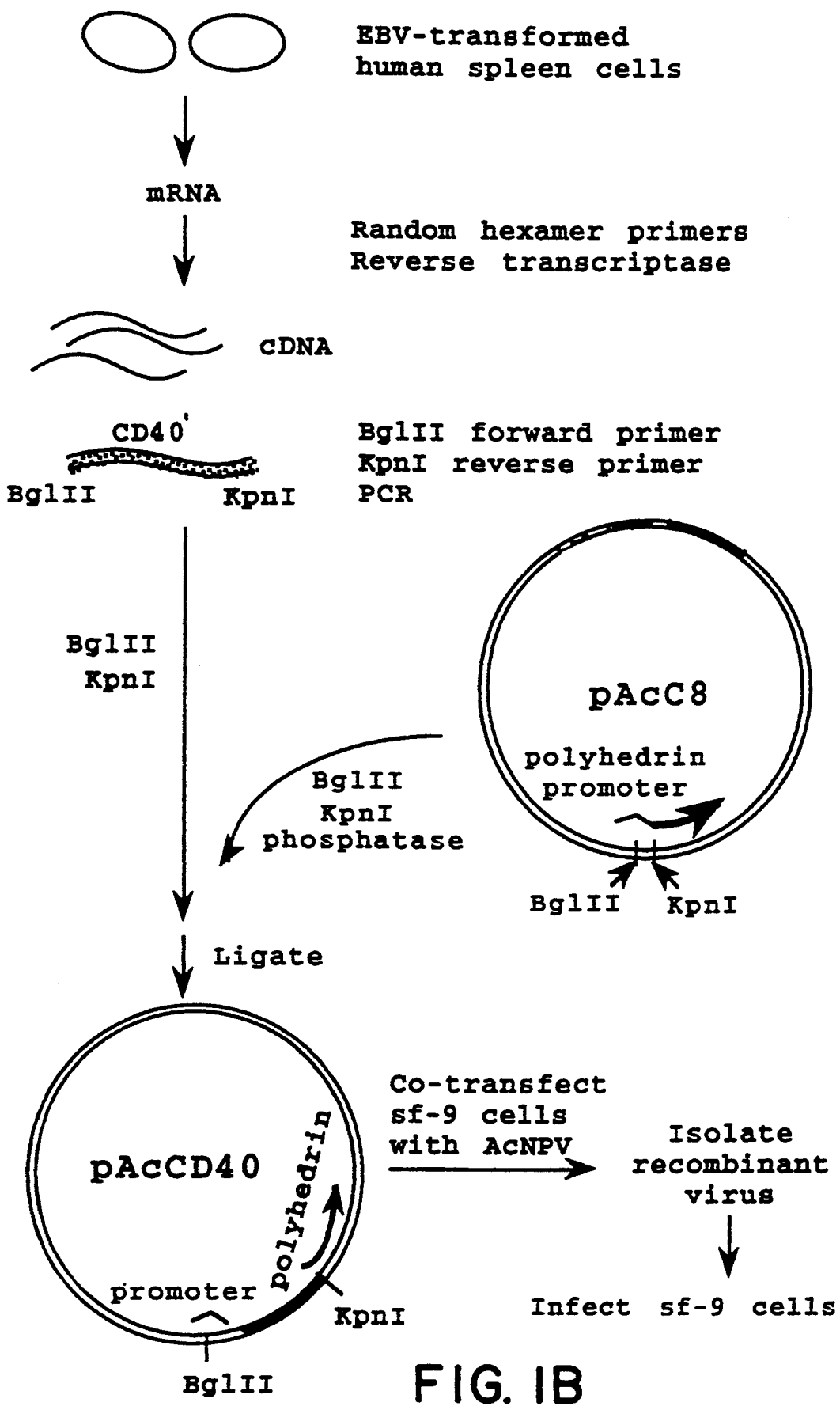

As used herein, the term "membrane-associated antigen", "cell surface molecule" and "cell surface antigen" all refer to a protein, polypeptide or peptide, where at least one antigenic portion of the protein, polypeptide or peptide is exposed on a surface of a biological membrane and which may have one or more of the following moieties covalently attached: one or more simple or complex sugar moieties (as in a glycoprotein), lipid moieties (as in a lipoprotein), a combination of lipid and sugar moieties, or other post-translational modifications.

Proteins are typically long chains of amino acid based polymers (polypeptides). Proteins may be composed of one, two or more polypeptide chains and may further contain some other type of substance in association with the polypeptide chain(s), such as carbohydrates. The size of proteins covers a rather wide range from (an arbitrary figure of) 5,000 to several hundred thousand g/mole. The 5,000 figure corresponds to the presence of roughly 40-45 amino acids. Proteins smaller than about 5,000 g/mole are typically referred to as polypeptides or simply peptides (Bohinski).

II. Generating Antibodies to Membrane-Associated Antigen Molecules

This section describes a method for generating and selecting antibodies to a cell surface molecule, using transfected insect cells as immunogen. The transfected insect cells of the present invention may also be used in screening assays.

According to an one embodiment, the invention includes a method for producing polyclonal antibodies to a cell surface antigen. The method involves the following steps: the immunization step, which includes (i) selecting and isolating a nucleic acid coding sequence which encodes the antigen of interest, (ii) inserting the coding sequence into a baculoviral expression vector so as to obtain efficient expression of the coding sequence, (iii) transfecting the expression vector into an insect cell line to obtain recombinant insect cells expressing the selected antigen, and (iv) immunizing a host animal with the insect cells expressing the membrane-associated antigen.

After immunization, the serum of the host animal is screened against cells, other than the insect cells, expressing the antigen of interest. Alternatively, membrane fractions containing the antigen of interest, or in some cases, purified recombinantly-produced antigens themselves can be used to screen the serum. Typically, (a) pre-bleed serum, (b) the serum of a host animal immunized with insect cells not expressing the antigen of interest, and (c) the serum of the host animal immunized with the recombinant insect cells are screened. The presence of antibodies specifically directed against the antigen of interest is indicated by negative reactions with sera (a) and (b), and positive reactions with serum (c).

According to another embodiment, the invention includes a method for the generation of hybridomas which produce monoclonal antibodies to a cell surface protein. The method involves the steps (i) to (iv) described above. After immunization of the host animal with the recombinant insect cells, antibody-producing cells are isolated from the animal. In a preferred embodiment of the invention, such antibody-producing cells are used to generate hybridoma cells, which are cloned and used for the production of monoclonal antibodies. Supernatants from such hybridoma cells are screened for specific antibody production, for example, using a cell-based screening assay described below.

A. Isolating Coding Sequences for Membrane Molecules

The nucleic acid coding sequence for a selected membrane-associated antigen can be isolated based on known amino acid and/or DNA coding sequences for the protein component of the antigen. The coding sequence can be isolated from biological sources by standard procedures (Ausubel, et al.; Maniatis, et al.; Sambrook, et al.) (e.g., hybridization, differential hybridization, cloning and plaque screening, etc.). Alternatively, synthetic oligonucleotide sequences encoding the antigen of interest can be prepared using commercially available automated oligonucleotide synthesizers or may be purchased, for example, from Synthetic Genetics (San Diego, Calif.). In the case of large coding sequences, the oligonucleotide coding sequence can be synthesized through a series of cloning steps involving a tandem array of multiple oligonucleotide fragments corresponding to the coding sequence (Crea; Yoshio et al.; Eaton et al.). Oligonucleotide coding sequences can be amplified and isolated by standard recombinant procedures (Maniatis et al.; Ausubel et al.) or by polymerase chain reaction (Mullis; Mullis, et al.).

When the sequence of the membrane-associated antigen is known or partially known a specific antigen coding sequence may be isolated. Typically, the antigen coding sequence is isolated from a cDNA library, generated by the insertion of DNA fragments from a selected source into a vector. The cDNA library containing DNA fragments from a membrane antigen-containing source can be constructed using random fragments cDNA molecules generated from target RNA molecules. Such a cDNA library is generally constructed using a bacterial system (such as lambda gt10 (Promega, Madison Wis.)), but can also be constructed in a yeast or eukaryotic expression system using conventional techniques (Ausubel).

The library is screened (usually by hybridization; Ausubel, et al.; Maniatis, et al.) for the presence of the membrane-associated antigen DNA sequence, typically using as a probe an oligonucleotide having a known or consensus sequence hybridizable with the antigen coding region. The probe can carrying a number of detection moieties including radioisotopes, biotin and digoxigenin. Alternatively, when a nucleic acid probe sequence is not available, screening for clones carrying the coding region of interest can be carried out using, for example, immunoscreening (using "PROTO-CLONE" lambda gt11 system, Promega; Young, et al.; Huynh, et al.).

Coding regions are isolated from recombinant isolates giving positive signals (either by hybridization or immunological screening). Typically, DNA fragments containing the coding regions are isolated by restriction digestion followed by size fractionation and fragment purification. Such nucleic acid coding regions may then be processed for insertion into a baculoviral transfer vector, such as the vector pAcC8 (FIG. 1A), as described in part B, below. Alternative baculovirus vectors are available including the vectors pVL1393 (Luckow et al.) and pAC3T3 (Summers et al.).

Alternately, coding sequences can also be isolated using polymerase chain reaction (PCR) amplification (Mullis; Mullis, et al.). Primers useful for the PCR can be derived from any known nucleic acid sequence. If the exact sequence is not known degenerative primers can be used (Mullis; Mullis, et al.). Typically these primers are two nucleic acid sequences consisting of 8 or more colinear nucleotides, where the two sequences are separate by some defined distance, in order to generate a target sequence (Example 1), and are complementary to opposite strands.

A typical PCR cycle involved the following steps: melting at elevated temperature, followed by annealing, and extension. The reactions are repeated for 25–30 cycles. The PCR products can be digested with restriction enzymes and electrophoretically resolved using a preparative 1.5% agarose gel. Clone-specific, amplified fragments are typically identified by electrophoretic gel size fractionation. The clone-specific DNA fragments are then recovered from the gel, for example, using the "GENE CLEAN" system (BIO 101, La Jolla Calif.). If necessary the DNA can be extracted with phenol and/or phenol:chloroform (1:1). Isolated DNA is ethanol precipitated. Following precipitation, the DNA is used for insertion into baculovirus expression vectors.

The generation of Sf9 cells expressing human CD40 or B7 antigens is schematically shown in FIG. 1B. As shown, RNA is isolated from a population of Epstein-Barr virus (EBV)-transformed human spleen cells, using standard procedures (Chirgwin, et al.). Total RNA is converted to cDNA using random hexamer priming, according to established methods, and as detailed in Example 1. The DNA molecule encoding the membrane-associated antigen molecules of interest is generated by PCR amplification, using forward and reverse primers having restriction sites for cloning at their 5' termini. Such cDNA primers, used in the preparation of coding regions for human CD40 and human B7 antigens are depicted in FIG. 2. These primers were constructed on the basis of the published complete DNA coding sequences for antigens B7 and CD40 (Freeman et al., 1989; Stamenkovic et al., 1989).

With continuing reference to FIG. 1B, the cDNA is mixed with a forward primer and a reverse primer, in the presence of a thermostable polymerase, such as polymerase obtained from *Thermus aquaticus*, a mixture of equimolar deoxynucleotides, and a buffer system (Example 1). The mixture is subjected to amplification in a thermocycler, and PCR products obtained are subcloned in the polylinker of a baculovirus transfer vector. One such vector, pAcC8, is diagrammatically represented in FIG. 1A. Any of a number of such baculoviral transfer vectors containing unique restriction endonuclease sites downstream of the polyhedrin promoter (Miller) can be utilized in the practice of the present invention: for *Autographica californica* nuclear polyhedrosis virus (AcNPV) (Wu, et al.; Matsuura, et al.; Takehara, et al.) or *Bombyx mori* nuclear polyhedrosis virus (pBmNPV) polyhedrin mRNA (Nyunoya, et al.; Sekine, et al.).

Before expression in baculovirus, DNA inserts are typically checked for PCR-induced mutations by sequencing analysis.

B. Inserting an Antigen Coding Sequence into a Baculoviral Vector

Insertion of the membrane-associated antigen coding region into a baculovirus vector is performed according to established procedures (Ausubel, et al.; Maniatis, et al.; Sambrook, et al.). Full length cDNAs encoding human B7 and human CD40 were generated by PCR using primers with restriction sites for cloning. The template for PCR amplification was cDNA generated from EBV-transformed human spleen B cell RNA.

Briefly, an isolated DNA coding region is ligated into the baculoviral transfer vector or plasmid, such as a pAcC8 plasmid, so that the membrane-associated coding region is down-stream of the polyhedron promoter. The polyhedron gene ATG has been mutated to ATT (FIG. 1A) to prevent translational initiation in recombinant clones that do not contain a coding sequence with a functional ATG. The resulting plasmid DNA is co-transfected with wild type baculovirus (AcNPV) into insect cells from *Spodoptera frugiperda* (Sf9 cells) to create recombinant virus particles, via in vivo recombination between the wild type virus and the recombinant vector, carrying the membrane-associated antigen gene.

Examples 1–2 describe the isolation of recombinant baculovirus vectors containing heterologous segments of DNA: pAcCD40 (encoding a full-length CD40 molecule), pAcCD40-ED/Glu (encoding the extracellular domain of CD40), pAcB7 (encoding a full-length B7 molecule) and pCcB7-ED/Glu (encoding the cellular domain of the B7 molecule).

C. Infecting Insect Cells with Baculoviral Vectors

The recombinant viruses described above were then used to co-infect insect cells (Example 2). These cells then expressed the antigens encoded by the heterologous DNA inserts.

Sf9 cells (*Spodoptera frugiperda*; Summers, et al.), at a density of $10^6$ cells/ml, were infected with recombinant virus. Recombinant baculovirus-infected Sf9 cells were identified and clonally purified (Summers et al.).

Cells expressing cell surface antigen were harvested after 48 hours and used for the immunization of host animals. For production of secreted recombinant proteins, the cells were harvested after 72 hours of culture.

Figure 3:
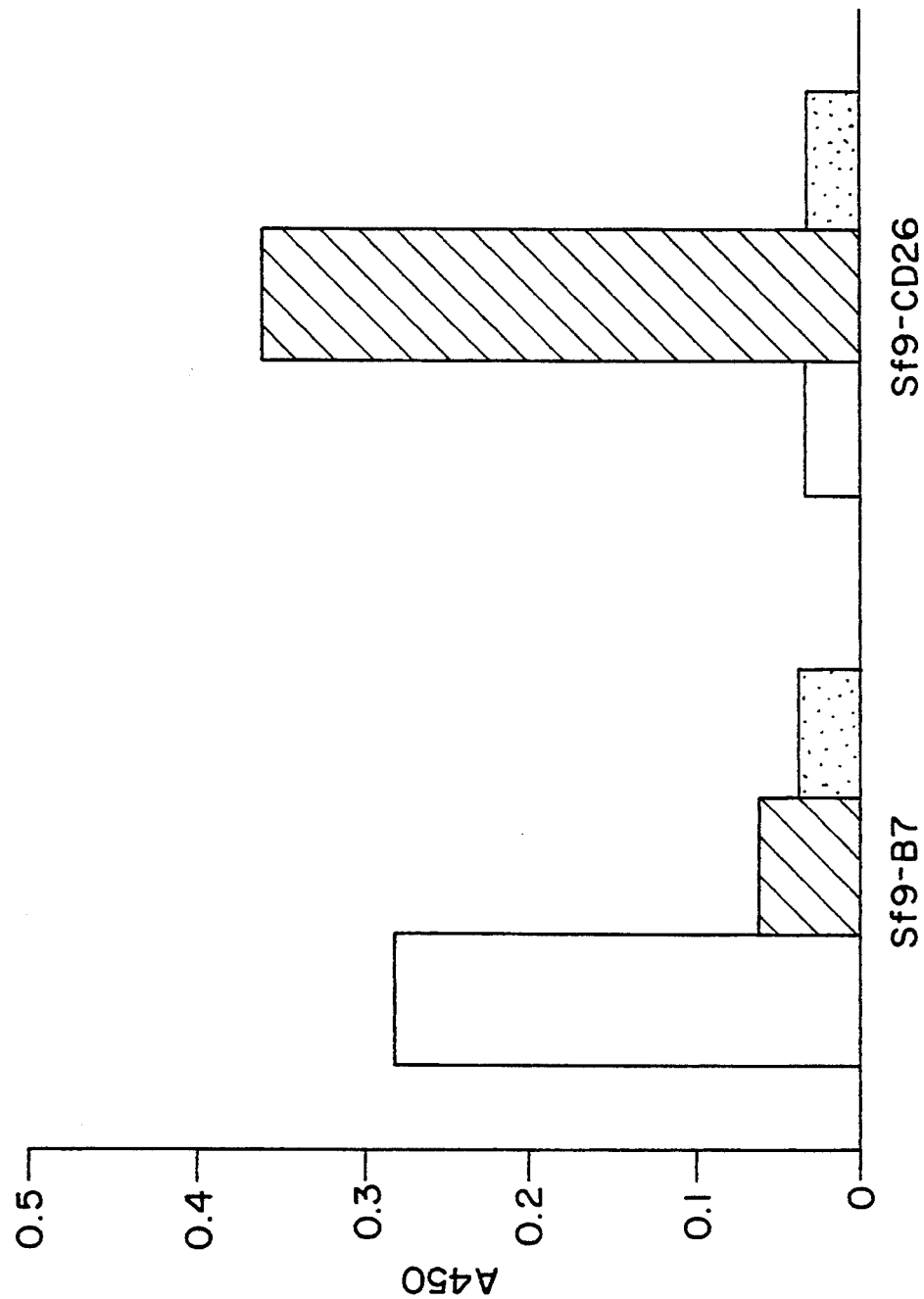
FIG. 3 shows the results of ELISA assays examining the reaction of anti-(B7) monoclonal antibody BB-1 with Sf9 cells infected with AcB7 virus and with Sf9 cells expressing human CD26.
Figure 4:
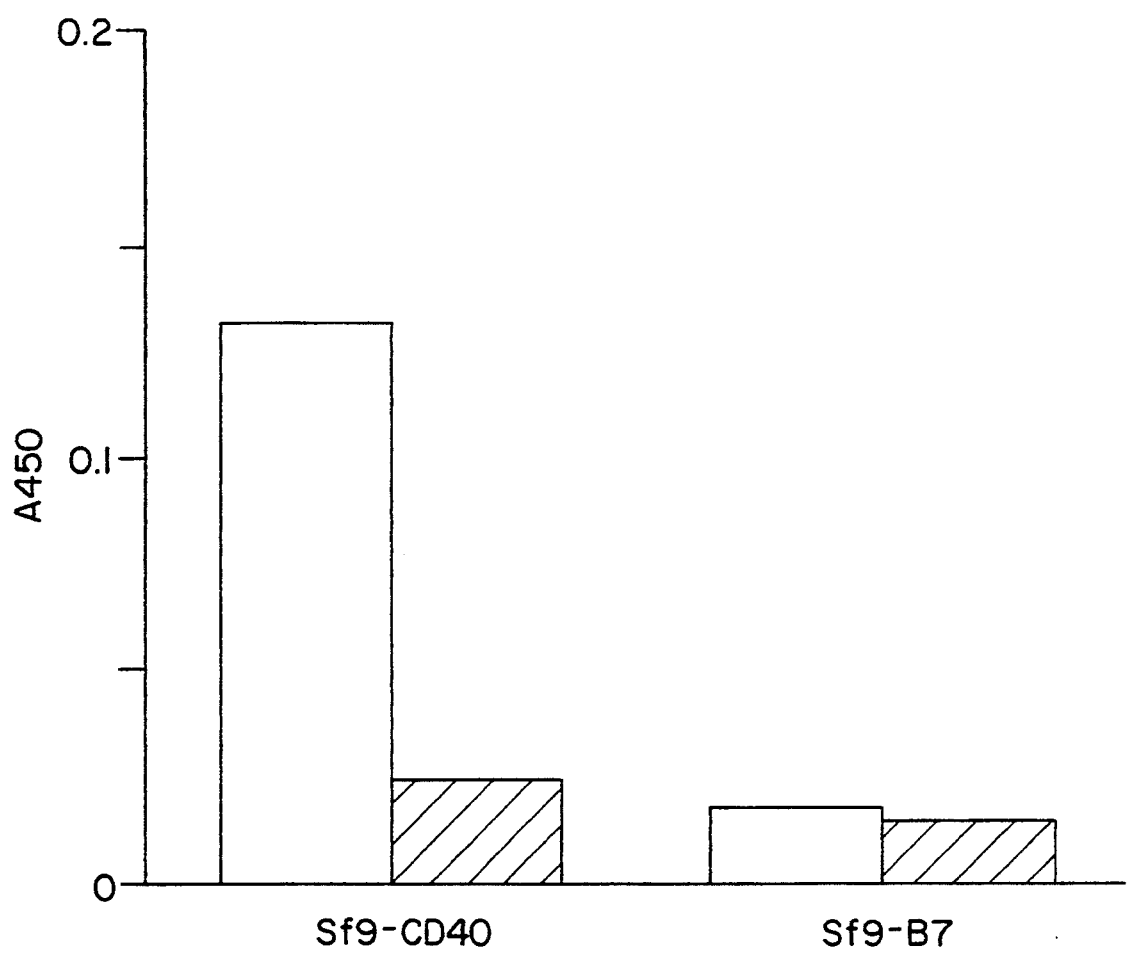
FIG. 4 the results of ELISA assays examining the reaction of anti-(CD40) monoclonal antibody S2C6 with Sf9 cells expressing CD40 and Sf9 cells expressing B7.

The expression of the recombinant molecules on the cell surface of the Sf9 cells (Example 3) was tested using an ELISA system (Harlow, et al.). FIG. 3 shows that the anti-(B7) monoclonal antibody BB-1 reacted only with Sf9 cells infected with AcB7 virus, but not with Sf9 cells expressing human CD26. In contrast, the anti-(CD26) monoclonal antibody Ta-1 reacted only with the Sf9 cells expressing CD40. FIG. 4 shows that the anti-(CD40) monoclonal antibody S2C6 reacted only with Sf9 cells expressing CD40, but not with Sf9 cells expressing B7. These results show the specificity of the method of the present invention for the production of selected membrane-associated antigens in the baculovirus system. These results also indicate that the membrane-associated antigens are exposed on the surface of the Sf9 cells.

Further, these results suggest that Sf9 cells expressing selected membrane-associated antigens can be used to screen sera and hybridoma supernatants for the presence of antibodies reactive against the selected antigen.

D. Injecting Insect Cells Expressing the Membrane-Associated Antigen into a Host Animal Appropriate host animals for the production of polyclonal antibodies include, for example, rabbits, goats, sheep, guinea pigs, chimpanzees and dogs. One advantage of the present invention is that immunization adjuvants are generally not required.

Appropriate host animals for use in the production of monoclonal antibodies commonly include rats, hamsters and mice. However, in cases where it is desirable to produce antibodies that are immunologically closer to humans, sources of such antibodies may include higher primates such as chimpanzees. Fusion with a heteromyeloma fusion partner can be used for the generation of monoclonal antibodies (Carroll; Perkins, 1991). Such fusions can be achieved by a number of methods known in the art (Harlow, et al.) including exposure of mixed cells to polyethylene glycol and exposure of cells to strong electric field (electrofusion). Hybridomas are selected by growth in selective medium, then are tested for antigen specificity as described below.

For the generation of monoclonal antibodies to CD40 and B7, mice were immunized (Example 5) with the Sf9 cells expressing these molecules on the cell surface. One week after the second immunization, the mice were bled and the sera were analyzed for the presence of specific antibodies using fluorescent cell staining of EBV-transformed B cells (Example 3). FIG. 5 shows the results of the cell staining which indicate that mice immunized with Sf9 cells expressing CD40 or B7 had a serum titre against EBV-transformed B cell line ARC (American Type Culture Collection (A.T.C.C.), 12301 Parklawn Dr., Rockville Md. 20852), which is positive for both CD40 and B7. In contrast, mice which were immunized with control Sf9 cells showed no reactivity with the ARC cells. The results indicate that host animals can be immunized with Sf9 cells expressing a membrane-associated antigen of choice and the immunization results in an immune response including antibodies against the recombinant antigen. The immunization does not result in antibodies cross-reactive with human proteins other than the recombinant human protein cloned in the Sf9 insect cells.

One mouse was given a final booster injection with CD40 expressing Sf9 cells and one with B7 expressing Sf9 cells. Three days after the booster injection, the spleens were removed and the splenocytes were fused with SP2/0 murine myeloma cells.

E. Isolating and Immortalizing Specific Antibody-Producing Lymphocytes

Antibody-producing lymphocytes for monoclonal antibody production are preferably B-lymphocytes, such as may be isolated from the bone marrow, spleen or lymph nodes of an immune host animal (Harlow, et al.).

Alternatively, B-lymphocytes can be isolated from the peripheral circulation. In this case, blood samples are centrifuged, and are subjected to gradient separation techniques to produce a crude peripheral blood lymphocyte (PBL) mixture. Monocytes and T-lymphocytes are selectively depleted from this cell mixture according to established procedures (Mishell). Such remaining cells may be subjected to a selection procedure, such as a "panning" procedure, in which those cells having affinity for the antigen are concentrated by selective capture by an affinity matrix containing the antigen. In the context of the present invention, such a matrix might comprise a cell which expresses the membrane-associated antigen.

When B-lymphocytes are isolated from the circulation as described above, transformation with a transforming virus, such as Epstein-Barr virus, may be advantageous. Transformed cells (lymphoblastoids) are dispensed in subculture wells and maintained in culture for several weeks, prior to testing for specific antibody production. Cultures exhibiting such specific antibody production are expanded and fused with species-appropriate myeloma partner cells using one or more standard fusion protocols, including polyethylene glycol, as described above, or electrofusion. Methods for isolation and immortalization of B-lymphocytes from various sources are known in the art.

In experiments carried out in support of the present invention, splenocytes from immunized mice were fused with SP2/0 murine myeloma cells using polyethylene glycol as previously described by de Boer et al. (1988). The hybridoma clones were processed as described in Example 6.

Table 1 (Example 6) gives a summary of the fusion data. After the CD40 fusion, only half of the cells were seeded in 480 wells. This resulted in 351 wells with hybridoma growth. After the B7 fusion, the cells were distributed in 960 wells and this fusion yielded 312 wells with hybridoma growth. Fourteen days after the fusions, supernatants of 12 wells were pooled and the pools were tested for the presence of antibodies reactive with ARC cells. FACS analysis revealed that 4 pools from the CD40 fusion and 1 pool from the B7 fusion were reactive with ARC cells. When individual supernatants from the positive pools were retested, 4 wells reactive with CD40 and 1 well reactive with B7 were identified. The cells from these positive wells were cloned by limiting dilution, and, after 3 rounds of cell growth, 4 stable anti-(CD40) hybridoma clones (CD40-3A8, CD40-3C6, CD40-5D12 and CD40-5 and 1 stable anti-(B7) hybridoma clone (B7-24) were established. These results indicate the ability to achieve stable hybridoma clones secreting monoclonal antibodies directed against a chosen membrane-associated antigen.

A number of methods for screening hybridoma fusions are available (Harlow, et al.), including: antibody capture, (i) using labeled antigen, e.g., radioactively labelled partially purified or purified antigen, (ii) whole or permeabilized cells, e.g., Sf9 cells expressing the recombinant antigen; and antigen capture, (i) antibody/antigen in solution, (ii) antibody/antigen solid phase.

G. Testing the Specificity of the Monoclonal Antibodies

EBV-transformed cells were used for the screening of the primary hybridoma supernatants and for screening of the subsequent products of the limiting dilution cloning. Several lines of evidence presented below suggest that 4 anti-(CD40) and 1 anti-(B7) monoclonal antibodies have been generated.

First, supernatants from all 5 hybridoma clones were reactive with ARC cells and other EBV-transformed B cell lines, but not with T cell lines HSB (A.T.C.C.) and CEMM (A.T.C.C.).

Second, competition binding experiments were performed using the monoclonal antibodies of the present invention and soluble forms of the target antigens (Example 7). Hybridoma supernatants were pre-incubated with soluble forms of CD40 and B7 (Example 7). Subsequently, the mixtures were added to ARC cells for fluorescent cell staining. The results of the competition experiment are shown in FIG. 6. The data show that soluble B7, but not soluble CD40, could block the binding of anti-(B7) monoclonal antibody B7-24 to ARC cells. Conversely, soluble CD40, but not soluble B7, could block the binding of anti-(CD40) monoclonal antibody CD40-3A8 to ARC cells. Similar results were obtained with the other 3 anti-(CD40) monoclonal antibodies. Furthermore, the effects of soluble CD40 on the anti-(CD40) monoclonal antibodies and the effect of soluble B7 on the anti-(B7) monoclonal antibody was concentration dependent. Decreasing the amount of soluble protein resulted in decreased blocking of binding of the antibodies to ARC cells.

For further analysis, the anti-(CD40) and anti-(B7) monoclonal antibodies were tested for their ability to bind to tonsillar B cells (Example 8). Table 2 shows that 89–95 percent of freshly isolated tonsillar B cells stained positive with the four anti-(CD40) monoclonal antibodies. About the same percentage of cells was positive with anti-(CD40) monoclonal antibody G28.5 (Clark, et al.). Table 3 shows that 12–17 percent of freshly isolated tonsillar B cells stained positive with anti-(B7) monoclonal antibody B7-24. However, when tonsillar B cells were cultured for 5 days in the presence of immobilized anti-(IgM) antibodies and IL-2, the percentage of cells positive for B7-24 increased up to about 25 percent.

Furthermore, when tonsillar B cells were stimulated with anti-(IgM) antibodies and IL-2, not only did the number of B cells positive for B7-24 increase, but there was also a significant increase in the amount of fluorescent staining per cell, indicating that the expression of B7 was increased after stimulation.

The above data indicate that the method of the present invention provides a way to isolate monoclonal antibodies which are specifically reactive with membrane-associated antigens. The monoclonal antibodies obtained by the method of the present invention can be typed as previously described (Harlow, et al.).

III. Utility

For the production of monoclonal antibodies it is optimal to immunize mice with purified material. However, purification of membrane antigens requires specialized and complex techniques, and furthermore, extraction from the membrane may alter the structure of the molecule. In addition, solubilization of proteins often decreases their immunogenicity. Therefore, most monoclonal antibodies to cell surface antigens have been obtained after immunization with mice with whole cells or membrane fractions. In many cases, specific lymphocyte subsets have been injected into mice resulting in panels of monoclonal antibodies. These antibodies have been used to isolate and characterize the antigen that they bound. When mice are immunized with whole cells, antibodies to a large number of different molecules are generated. It is therefore difficult to use the same cells for the screening of specific antibody production by the hybridoma clones.

To circumvent the above-mentioned problem, the method of the present invention involves the expression of membrane-associated antigens in insect cells and the use of these insect cells to immunize host animals. Since the introduction of PCR technology (Saiki et al., 1985; Saiki et al., 1988; Mullis; Mullis, et al.), it has become relatively straight-forward to clone cDNAs for proteins whose coding nucleic acid coding sequence has been published. One can use PCR primers spanning the complete coding region only, and incorporate restriction sites in these primers to facilitate cloning into expression vectors.

It has been shown that human intracellular, secreted and transmembrane proteins can be expressed at high levels in insect cells when expressed in the cells under the regulation of the non-essential baculovirus gene for the polyhedrin protein (Webb et al., 1989; reviewed by Luckow, 1990). Experiments performed in support of the present invention have shown that only 2 injections with $5 \times 10^6$ Sf9 cells expressing human CD40 or human B7 gave good serum titres against these antigens. Furthermore, the insect cells themselves did not evoke an immune response cross reactive with human cells. This enabled the use EBV transformed B cells for the screening of specific antibody production by the hybridoma clones, with minimal risk of obtaining false positives. All of the positive primary wells obtained by the method of the present invention were in fact specific for the antigen that was used for immunization.

Antibodies obtained by the method of the present invention, directed against membrane-associated antigens, are advantageous for use as diagnostic agents for the detection of the membrane-associated antigen. For example, antibodies directed against cell-surface marker proteins or viral proteins protruding from the cell surface.

One diagnostic configuration involves use of anti-viral antibodies capable of detecting viral specific antigens. The antigens may be detected, for example, using an antigen capture assay where viral antigens present in candidate serum samples are reacted with an antigen-specific monoclonal or polyclonal antibody. The antibody is bound to a solid substrate and the antigen is then detected by a second, different labelled antibody directed against the anti-viral antibody.

The anti-viral antibodies obtained by the method of the invention can be used as a means of enhancing an anti-viral immune response since antibody-virus complexes are typically recognized by macrophages and other effector cells. The antibodies can be administered in amounts similar to those used for other therapeutic administrations of antibody. For example, pooled gamma globulin is administered at 0.02–0.1 ml/lb body weight during the early incubation of viral diseases such as rabies, measles and hepatitis B to interfere with viral entry into cells. Thus, antibodies reactive with a membrane-associated viral antigen can be passively administered alone, in a "cocktail" with other anti-viral antibodies, or in conjunction with another anti-viral agent to enhance the immune response and/or the effectiveness of an anti-viral drug.

The following examples illustrate, but in no way are intended to limit, the present invention.

Materials and Methods

Iscove's modification of Dulbecco's Eagle medium (IMDM) and foetal bovine serum were obtained from JR Biosciences (Lenexa, Kans.); penicillin and streptomycin were obtained from Irvine (Santa Ana, Calif.); and polyethylene glycol (mol. wt. 1500) was obtained from Boehringer Mannheim (Indianapolis, Ind.).

Culture Media. SP2/0 murine myeloma cells, hybridoma cells and cell lines were cultured in IMDM supplemented with streptomycin (200 µg/ml), penicillin (200 U/ml) and 10% heat inactivated foetal bovine serum (complete IMDM). The Sf9 insect cells were cultured in shaker flasks agitated (125–150 rpm) in medium described by Maiorella et al. (1989) supplemented with 0.5% foetal bovine serum.

Antibodies. Anti-(human B7) monoclonal antibody BB-1 (Yokochi et al., 1982) was obtained from Dr. E. A. Clark (University of Washington, Seattle, Wash.) and was used as purified antibody. Anti-(human CD40) monoclonal antibody G27.5 (Clark et al., 1986) was obtained from Dr. J. A. Ledbetter (Oncogen Corporation, Seattle, Wash.) and was used as purified antibody. Anti-(CD40) monoclonal antibody S2C6 (Paulie et al., 1985) was obtained from Dr. S. Paulie (University of Stockholm, Stockholm, Sweden) and was used as purified antibody. Anti-(human CD26) monoclonal antibody Ta-1 and anti-(CD20) monoclonal antibody B1 were obtained from Coulter (Hialeah, Fla.). Anti-(CD3) monoclonal antibody OKT3 was obtained from Ortho (Raritan, N.J.), and the anti-(LeuM3) monoclonal antibody was obtained from Becton-Dickinson (San Jose, Calif.). Anti-(IgM) antibodies coupled to beads (Immunobeads) were obtained from Bio-Rad (Richmond, Calif.).

The monoclonal antibodies of the present invention can be labeled, by standard methods, using a number of reporter moieties, including the following: fluorescent labels (fluorescein (FITC), R-phycoerythrin, rhodamine (TMRITC), rhodamine 600 (XRITC), "TEXAS RED," and the like, commonly avidin linked); radioactive moieties ($^{125}I$ and the like); light-emitting (luciferase and the like); enzymatic (horseradish peroxidase, alkaline phosphatase, glucose oxidase, $\beta$-galactosidase, and the like). Further, reporter antibodies (antibodies which have binding specificity for the monoclonal antibodies of the present invention, e.g., goat anti-mouse IgG) can also use the above-listed labelling moieties.

*E. coli* DNA polymerase I (Klenow fragment) was obtained from Boehringer Mannheim Biochemicals (BMB) (Indianapolis, Ind.). T4 DNA ligase and T4 DNA polymerase were obtained from New England Biolabs (Beverly, Mass.); Nitrocellulose filters are obtained from Schleicher and Schuell (Keene, N.H.).

Synthetic oligonucleotide linkers and primers were prepared using commercially available automated oligonucleotide synthesizers. Alternatively, custom designed synthetic oligonucleotides may be purchased, for example, from Synthetic Genetics (San Diego, Calif.). cDNA synthesis kit and random priming labeling kits are obtained from Boehringer-Mannheim Biochemical (BMB, Indianapolis, Ind.).

Oligonucleotide sequences encoding peptides can be either synthesized as described above. Alternatively, peptides can be synthesized directly by standard in vitro techniques (Applied Biosystems, Foster City Calif.).

Common manipulations involved in polyclonal and monoclonal antibody work, including antibody purification, were performed by standard procedures (Harlow, et al.).

Example 1

PCR Cloning of CD40 and B7

RNA was isolated from a population of EBV-transformed human spleen cells essentially as described by Chirgwin et al. (1979). In brief, the cells were washed twice with phosphate buffered saline (PBS) and lysed in 5M guanidinium thiocyanate in the presence of 0.7M 2-mercaptoethanol. The cell lysate was layered on a discontinuous CsCl gradient (Chirgwin, et al.) and centrifuged for 16 hours at 26,000 rpm in a Beckman SW28 rotor. The RNA was recovered by dissolving the pellet in DEPC-treated $H_2O$. The RNA was precipitated with ethanol once, resuspended in DEPC treated $H_2O$, and stored at $-70°$ C.

Total RNA (10 $\mu$g/reaction) was converted to cDNA using random hexamer priming in 50 $\mu$l reaction buffer containing 500 units LMV-RT (Bethesda Research Laboratories, Bethesda, Md.), 5 $\mu$M random hexamers (Pharmacia, Piscataway, N.J.), 1 mM DTT, dNTP mix (0.5 mM each), 10 mM Tris-HCL pH 8.3, 50 mM KCl, 2.5 mM $MgCl_2$ and 0.1 mg/ml BSA (bovine serum albumin). After incubation at 37° C. for 1 hour, the samples were boiled for 3 min and stored at $-70°$ C. The DNA encoding the CD40 and B7 molecules was generated by PCR using primers which contained sequences having homology to known CD40 and B7 sequence, where the primers also encoded restriction sites useful for cloning (FIG. 2). These primers were based on the published cDNA coding sequences for B7 and CD40 (Freeman et al., 1989; Stamenkovic et al., 1989). All primers start with a C-G clamp at the 5' end followed by a restriction site for cloning (shown in bold, FIG. 2). The underlined sequences in the backward primers, for the cloning of the soluble forms of B7 and CD40, represents an epitope recognized by a monoclonal antibody used for affinity purification. The numbers in brackets represent the location of the primers relative to the published cDNAs for CD40 and B7.

For PCR amplification, 1 $\mu$l of cDNA was mixed 1 $\mu$l (10 picomoles) of a forward primer, 1 $\mu$l (10 picomoles) of a backward primer, and 47 $\mu$l of PCR mix. The PCR mix consisted of 1.25 units Taq polymerase (Perkin-Elmer/Cetus, Norwalk, Conn.), dNTP mix (0.2 mM each), 10 mM Tris-cHL pH 8.3, 50 mM KCl, 2.5 mM $MgCl_2$ and 0.1 mg/ml BSA. The 50 $\mu$l of PCR mixture was overlaid with 70 $\mu$l mineral oil and subjected to 25 cycles of amplification in a Perkin-Elmer/Cetus thermocycler (denaturation at 95° C. for 30 sec, primer annealing at 55° C. for 30 sec and extension at 72° C. for 1.5 min). PCR products were obtained after 25 amplification cycles.

The amplification products were digested with BglII and KpnI (FIG. 1B) and isolated by size-fractionation. Before expression in baculovirus, the DNA sequence of each fragment was confirmed by sequencing analysis to prevent the introduction of PCR-induced mutations. The baculovirus transfer vector pAcC8 was also digested with BglII and KpnI (FIG. 1B).

The amplified fragments were ligated to the linear pAcC8 vector (ratio of insert to vector was 3:1). The ligation products were transformed into bacterial strain DH5$\alpha$ (Gibco/BRL, Gaithersburg Md.) and recombinant pAcC8 vectors were selected on the basis of ampicillin resistance. Recombinant plasmids were isolated from bacterial clones (Maniatis, et al.; Ausubel, et al.) and the presence of the insert of interest verified using polymerase chain reactions (see above). Large scale plasmid preparation was performed by standard procedures (Ausubel, et al.; Maniatis, et al.; Sambrook, et al.).

Example 2

Baculovirus Expression of Human CD40 and B7

Sequences encoding human CD40 and human B7 were recombined into the *Autographa californica* baculovirus (AcNPV) using the transfer vectors pAcCD40 (encoding the full-length CD40 molecule), pAcCD40-ED/Glu (encoding the extracellular domain of CD40), pAcB7 (encoding the full-length B7 molecule) and pCcB7-ED/Glu (encoding the cellular domain of the B7 molecule).

The plasmids were cotransfected with wild-type baculoviral DNA (2–10 pfu) (AcNPV; Summers et al.) into SF9 (*Spodoptera frugiperda*) cells at a density of $10^6$ cells/ml (Summers et al.). Recombinant baculovirus-infected Sf9 cells were identified and clonally purified (Summers et al.).

For cell surface expression of recombinant proteins the cells were harvested after 48 hours of culture; for the production of secreted recombinant proteins, the cells were harvested after 72 hours of culture.

Example 3

Sf9 Cell ELISA

Sf9 insect cells infected with recombinant virus were cultured for 48 hours in 24-well plates. After removal of the tissue culture medium the plates were incubated for 45 min at room temperature (RT) with 0.25 ml of antibody in PBS with 1% BSA (PBS-BSA). After three washed with PBS-BSA, the plates were incubated for 35 min at RT with 250 μl of a 1/250 dilution of goat anti-(mouse total Ig) immunoglobulins conjugated to horseradish peroxidase (Zymed, South San Francisco, Calif.) in PBS-BSA. Unbound peroxidase activity was removed by washing five times with PBS-BSA. Bound peroxidase activity was revealed by the addition of an assay mixture prepared by diluting 0.5 ml of 2 mg/ml 3,3',5,5'-tetramethylbenzidine in ethanol to 10 ml with 10 mM Na acetate, 10 mM EDTA buffer (pH 5.0) and adding 0.03% (v/v) $H_2O_2$. The reaction was stopped after 10 min by adding 100 μl of 1M $H_2SO_4$.

The above-described ELISA assays performed on live Sf9 cells gave the following results. FIG. 3 presents the data for Sf9 cells infected with pAcB7 and pAcCD26 which were cultured for 48 hours in 24-well plates. The antibodies used in the ELISA were: B7-24, anti-(B7) (open bars), Ta-1, anti-(CD26) (hatched bars) and no primary antibody (gray bars).

FIG. 4 presents the data for live Sf9 cells infected with pAcB7 and pAcCd40 which were cultured for 48 hours in 24-well plates. The antibodies used in the ELISA were: S2C6, anti-(CD40) (open bars) and no primary antibody (hatched bars).

Example 4

Fluorescent Cell Staining

A. Fluorescent Cell Staining.

Cells ($10^6$/sample) were incubated in 10 μl primary antibody (10 μg/ml in PBS-BSA or HBSS (Hanks' Balanced Salt Solution, Gibco/BRL) supplemented with 1% BSA and 0.05% sodium azide) for 20 min at 4° C. After 3 washes with PBS-BSA or HBSS-BSA, the cells were incubated in 100 μl FITC-labeled Fab '2 fragments of goat anti-(mouse IgG)antibodies (Jackson, West Grove, Pa.) for 20 min at 4° C. After 3 washes with PBS-BSA or HBSS-BSA and 1 wash with PBS, the cells were resuspended in 0.5 ml PBS. Analyses were performed with a FACSSCAN V (Becton Dickinson, San Jose, Calif.).

General protocols for flow cytometric analysis and clinical data analysis for flow cytometry are detailed in Keren et al. and Coon et al. General blood cell counting techniques and DNA quantitation are described by Powers, Keren et al., and Coon et al.

Figure 5A:
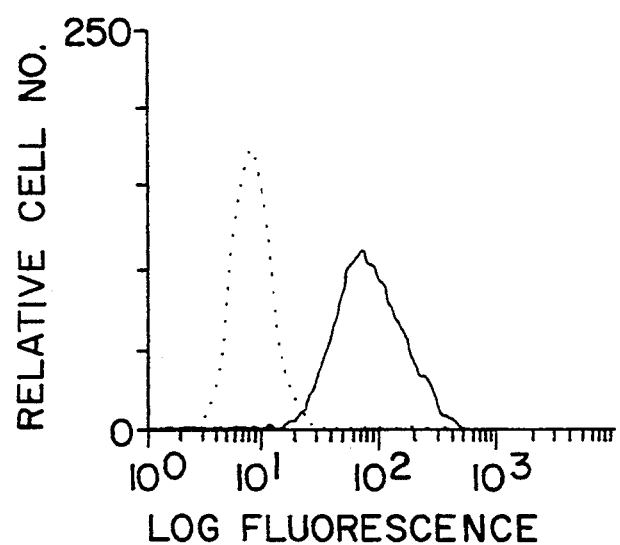
FIGS. 5A–5C shows the results of the fluorescent cell staining of EBV-transformed B cell line ARC cells expressing CD40 or B7.

The data for fluorescent cell staining of ARC EBV transformed B cells is presented in FIG. 5. In FIG. 5A, the results for staining at 1:100 dilution of serum from a mouse immunized with B7 expressing Sf9 cells (solid line) or a 1:100 dilution of normal mouse serum (dotted line) are shown.

Figure 5B:
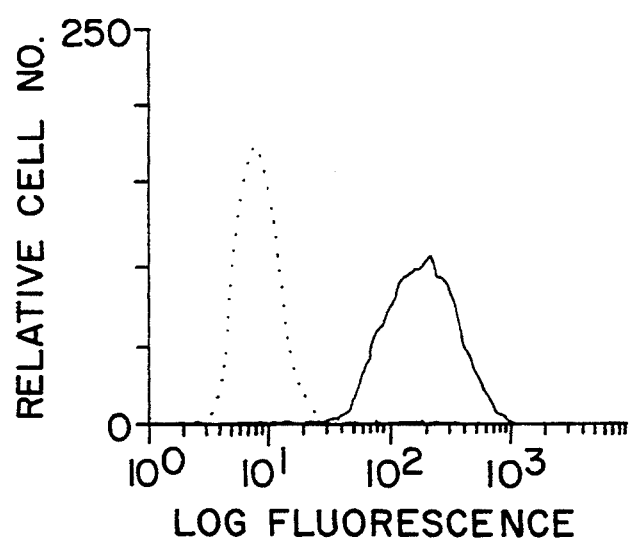

In FIG. 5B, the results for staining with a 1:100 dilution of serum from a mouse immunized with CD40 expressing Sf9 cells (solid line) or a 1:100 dilution of normal mouse serum (dotted line) are shown.

Figure 5C:
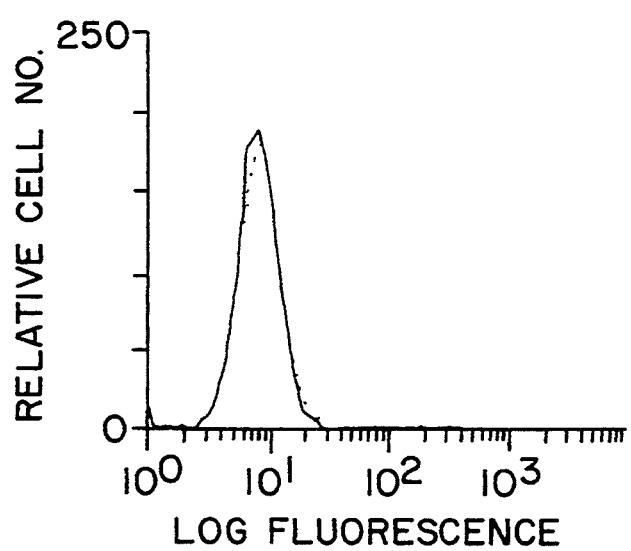

In FIG. 5C, the results for staining with a 1:100 dilution of serum from a mouse immunized with control Sf9 cells (solid line) or a 1:100 dilution of normal mouse serum (dotted line) are shown.

B. Soluble Antigen Competition Assays.

ARC EBV-transformed B cells were stained with anti-(B7) and anti-(CD40) monoclonal antibodies in the presence and absence of soluble B7 and soluble CD40. The antibodies and the soluble B7, soluble CD40 or controls were preincubated at RT for 20 min before addition to the ARC cells.

Figure 6A:
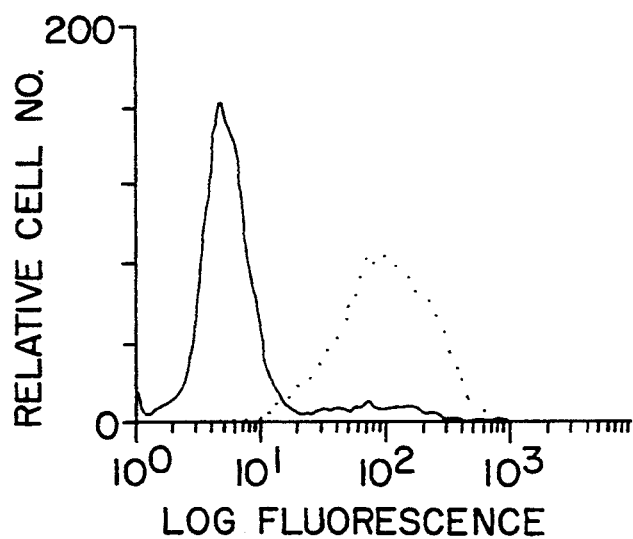
FIGS. 6A–6F show the results of competition assays using fluorescent cell staining of EBV-transformed B cell line ARC cells expressing CD40 and B7, as well as soluble CD40 and B7 antigens.
Figure 6B:
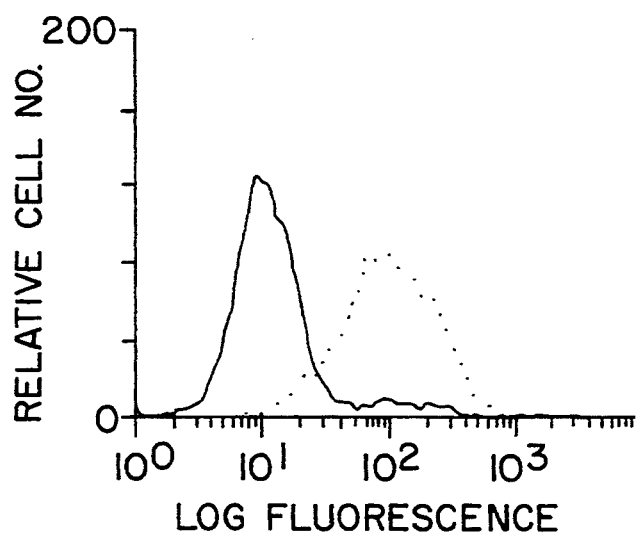
Figure 6C:
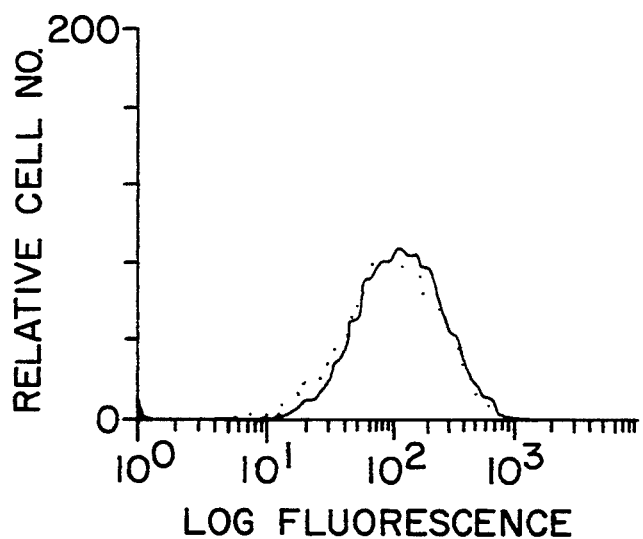
Figure 6D:
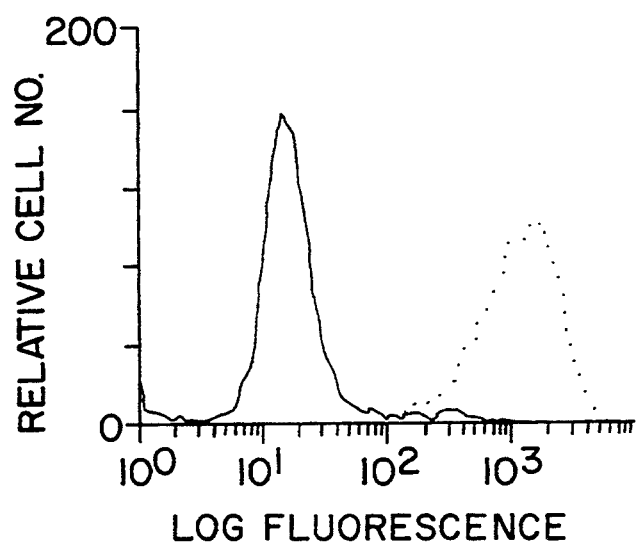
Figure 6E:
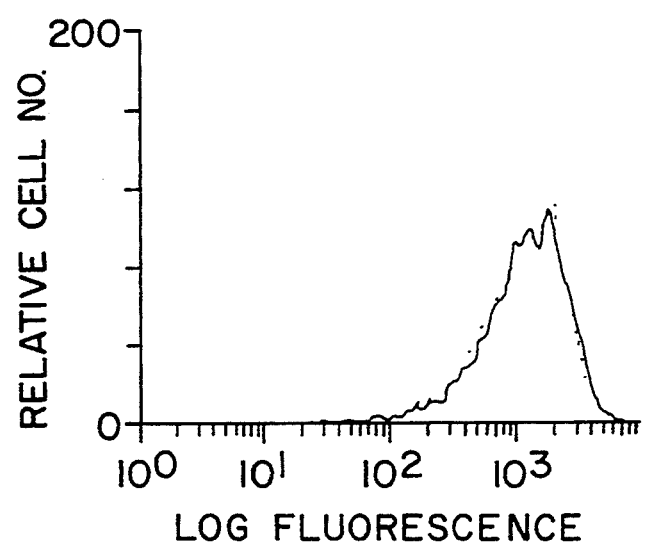
Figure 6F:
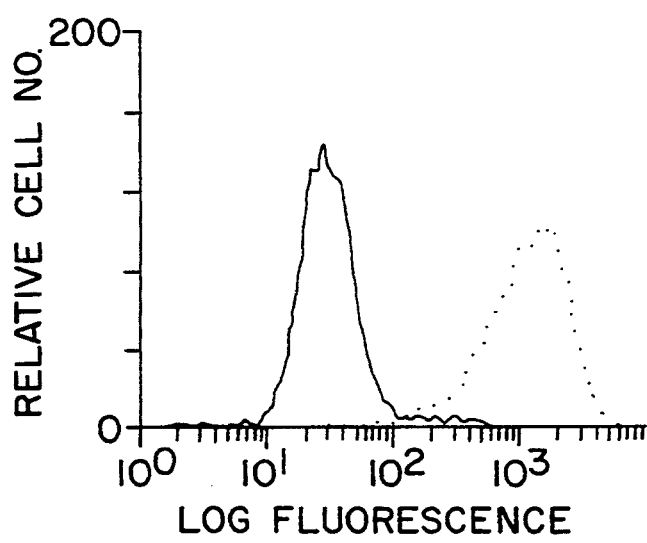

FIG. 6A shows the results of staining with B7-24 (dotted line) or secondary antibody only (solid line). FIG. 6B shows the results of staining with B7-24 alone (dotted line) or B7-24 preincubated with soluble B7 (solid line). FIG. 6C shows the results of staining with B7-24 alone (dotted line) or B7-24 preincubated with soluble CD40. FIG. 6D shows the results of staining with CD403A8 (dotted line) or second antibody alone (solid line). FIG. 6E shows the results of staining with CD407A8 alone (dotted line) or CD403A8 preincubated with soluble B7 (solid line). FIG. 6F shows the results of staining with CD403A8 alone (dotted line) or preincubated with soluble CD40 (solid line).

Example 5

Host Animal Immunization

Female BALB/c mice were injected intraperitoneally at day 0 and day 14 with $5 \times 10^6$ Sf9 cells infected with AcCD40 virus, AcB7 virus or AcCd3 virus (control virus). At day 21, 100 μl of serum was obtained to test for the presence of specific antibodies. After a rest period of at least two weeks, the mice received a final injection with $5 \times 10^6$ cells infected with AcCD40 or AcB7 virus. Three days after this last injection, the spleen cells were used for cell fusion.

Example 6

Generation of Hybridoma Clones

Splenocytes from immunized BALB/c mice were fused with SP2/0 murine myeloma cells at a ratio of 10:1 using 50% polyethylene glycol as previously described by de Boer et al. (1988). The fused cells were resuspended in complete IMDM medium supplemented with hypoxanthine (0.1 mM), aminopterin (0.01 mM), thymidine (0.016 mM) and 0.5 ng/ml hIL-6 (Genzyme, Cambridge, Mass.). The fused cells were then distributed between the wells of 96-well tissue culture plates, so that each well contained 1 growing hybrid on average.

After 10–14 days the supernatants of the hybridoma populations were screened for specific antibody production. For the screening of specific antibody production by the hybridoma clones, the supernatants of 12 wells were pooled and used for fluorescent cell staining of EVB-transformed B cells as described in Example 4. Subsequently, the supernatants of the positive pools were tested individually. Positive hybridoma cells were cloned three times by limiting dilution in IMDM/FBS containing 0.5 ng/ml hIL-6. The results of the analysis are presented in Table 1.

TABLE 1

| Summary of Fusion Data for the Generation of Monoclonal Antibodies to Human CD40 and Human B7 | | |
|---|---|---|
| Fusion: | Anti-CD40 | Anti-B7 |
| No. of wells seeded after fusion | 480[a] | 960 |
| No. of wells with hybridoma growth | 351 | 312 |
| No. of positive wells[b] | 4 | 1 |

TABLE 1-continued

Summary of Fusion Data for the Generation of Monoclonal Antibodies to Human CD40 and Human B7

| Fusion: | Anti-CD40 | Anti-B7 |
|---|---|---|
| Frequency of positive wells[c] | 1.15 | 0.31 |

[a]Only half of the cells obtained after fusion were analyzed.
[b]As determined by FACS analysis described in Example 4.
[c]The frequency of positive wells is defined as the number of positive wells divided by the total number of wells with hybridoma growth, multiplied by 100.

Example 7

Testing of Tonsillar B Cells

Tonsillar B lymphocytes were isolated from tonsils obtained from children undergoing tonsillectomy as described by deGroot et al. (1990). Briefly, the tissue was dispersed with scalpel blades, phagocytic cells and NK cells were depleted by treatment with 5 mM L-leucine methyl ester and T cells were removed by one cycle of rosetting with sheep erythrocytes treated with 2-aminoethyl isothiouronium bromide.

The anti-(CD40) and anti-(B7) monoclonal antibodies, were tested for their ability to bind to tonsillar B cells using the fluorescent cell staining assay described above in Example 4. For fluorescent stain analysis of cultured tonsillar B cells, propidium iodine was used to exclude dead cells.

Table 2 shows the results of the above analysis for the binding of anti-(CD40) monoclonal antibodies to highly enriched tonsillar B cells.

TABLE 2

Binding of Anti-(CD40) Monoclonal Antibodies to Highly Enriched Tonsillar B Cells

| Antibody | Specificity | % of Positive Cells[a] |
|---|---|---|
| OKT3 | CD3 | 2.1 |
| LeuM3 | LeuM3 | 2.5 |
| B1 | CD20 | 88.0 |
| G28.5 | CD40 | 92.1 |
| CD40-5H7 | CD40 | 93.7 |

TABLE 2-continued

Binding of Anti-(CD40) Monoclonal Antibodies to Highly Enriched Tonsillar B Cells

| Antibody | Specificity | % of Positive Cells[a] |
|---|---|---|
| CD40-5D12 | CD40 | 95.0 |
| CD40-3C6 | CD40 | 88.9 |
| CD40-3A8 | CD40 | 93.3 |

[a]The percentage of positive tonsillar cells was measured by fluorescent cell staining as described in Example 4.

These data show that 89-95 percent of freshly isolated tonsillar B cells stained positive with the four anti-(CD40) monoclonal antibodies.

The reaction of the tonsillar B cells with monoclonal antibody G28.5 (Clark, et al.) were tested in essentially the same manner: about the same percentage of cells were positive with G28.5 as with the anti-(CD40) monoclonals of the present invention.

Table 3 shows the results of binding of anti-(B7) monoclonal antibody B-7-24 to highly enriched tonsillar B cells as determined by the fluorescent cell labelling described in Example 4.

TABLE 3

Binding of Anti-(B7) Monoclonal Antibody B7-24 to Highly Enriched Tonsillar B Cells

| Antibody | Specificity | % of Positive Cells[a] | |
|---|---|---|---|
| | | Donor 1 | Donor 2 |
| OKT3 | CD3 | 8.0 | 2.1 |
| B1 | CD20 | 74.0 | 88.0 |
| B7-24 | B7 | 12.6 | 16.8 |

[a]The percentage of positive tonsillar cells was measured by fluorescent cell staining as described in Example 4.

These data show that 12-17 percent of freshly isolated tonsillar B cells stained positive with anti-(B7) monoclonal antibody B7-24.

While the invention has been described with reference to specific methods and embodiments, it will be appreciated that various modifications and changes may be made without departing from the invention.

It is claimed:

1. A method of generating an immortalized cell line producing a monoclonal antibody specific against a selected membrane-associated antigen, comprising producing the membrane-associated antigen on the cell surface of insect cells, injecting said insect cells into a host animal, recovering from the host animal cells capable of producing antibody molecules, immortalizing such cells for growth in cell culture, screening the immortalized cells for production of antibodies specific to the membrane-associated antigen in a binding assay employing non-insect cells having the membrane-associated antigen on the surface of the non-insect cells, and selecting those immortalized cells producing antibodies which bind to the membrane-associated antigen on the surface of said non-insect cells.

2. The method of claim 1, wherein said producing step further comprises inserting DNA encoding the membrane-associated antigen operatively into a baculoviral vector suitable for expression of said antigen in selected insect cells, transfecting insect cells with the vector, and selecting insect cells transformed with the vector which produce the membrane-associated antigen on the cell surface of the insect cells.

3. The method of claim 2, wherein said DNA is isolated using polymerase chain reaction performed on either RNA or DNA samples.

4. The method of claim 1, wherein the insect cells are obtained from *Spodoptera frugiperda*.

5. The method of claim 1, wherein said host animal cells capable of producing antibody molecules are either splenic cells or lymphocytes.

6. The method of claim 5, wherein said host animal cells are splenic cells and immortalization of the splenic cells is accomplished by fusion of the splenic cells to myeloma cells.

7. The method of claim 5, wherein said host animal cells are lymphocyte cells and immortalization of said lymphocyte cells is accomplished by transformation with Epstein Barr Virus.

8. The method of claim 1, where the host animal is a mouse.

9. The method of claim 1, where the non-insect cells having the membrane-associated antigen on the surface of the non-insect cells are human cells.

10. The method of claim 9, wherein said human cells are primary cells or passaged cells.

11. The method of claim 10, where said human cells are cultured lymphocytes.

12. The method of claim 11, where said lymphocytes are transformed B cells.

13. The method of claim 1, wherein the membrane-associated antigen is a human cell surface protein.

14. The method of claim 13, wherein the membrane-associated antigen is an antigenic marker protein for a peripheral blood mononuclear cell.

15. The method of claim 14, wherein the antigenic marker protein is either CD40 or B7.

16. The method of claim 1, wherein the membrane-associated antigen is a vital antigenic protein present on the surface of a human cell.

17. A method of producing sera containing antibodies specific against a selected membrane-associated antigen, comprising producing the membrane-associated antigen on the cell surface of insect cells, injecting said insect cells into a host animal, and screening sera from said animal for production of antibodies specific to the membrane-associated antigen in a binding assay employing non-insect cells having the membrane-associated antigen on the cell surface.

* * * * *